US008716171B2

(12) United States Patent
Kang et al.

(10) Patent No.: US 8,716,171 B2
(45) Date of Patent: May 6, 2014

(54) METHOD OF MANUFACTURING A POROUS GALLIUM (III) OXIDE PHOTOCATALYST FOR PREPARATION OF HYDROCARBONS

(75) Inventors: Jeung-Ku Kang, Daejeon (KR); Hang-Ah Park, Daejeon (KR); Jung-Hoon Choi, Daejeon (KR); Kyung-Min Choi, Daejeon (KR); Dong-Ki Lee, Daejeon (KR)

(73) Assignee: Korea Advanced Institutte of Science and Technology, Daejon (KR)

( * ) Notice: Subject to any disclaimer, the term of this patent is extended or adjusted under 35 U.S.C. 154(b) by 0 days.

(21) Appl. No.: 13/527,351

(22) Filed: Jun. 19, 2012

(65) Prior Publication Data
US 2013/0192975 A1 Aug. 1, 2013

(30) Foreign Application Priority Data

Jan. 27, 2012 (KR) .................. 10-2012-0008307

(51) Int. Cl.
*B01J 13/00* (2006.01)
*B01J 23/00* (2006.01)
*B01J 23/08* (2006.01)
*B01F 3/00* (2006.01)
*C09K 3/00* (2006.01)
*B01F 17/00* (2006.01)

(52) U.S. Cl.
USPC .............................. 502/300; 502/355; 516/9

(58) Field of Classification Search
USPC .................... 502/300, 355; 516/9; 204/628
See application file for complete search history.

(56) References Cited

U.S. PATENT DOCUMENTS

| 6,328,947 | B1 * | 12/2001 | Monden et al. ............... 502/355 |
| 6,348,631 | B1 * | 2/2002 | Desmurs et al. ............ 204/157.6 |
| 7,005,118 | B2 * | 2/2006 | Terres Rojas et al. ........ 423/702 |
| 7,585,811 | B2 * | 9/2009 | Nakamura et al. ............ 502/355 |

OTHER PUBLICATIONS

"Synthesis and Characterization of Gallium Oxide Nanostructures via a Soft-Chemistry Route," Yanyan Zhao et al. J. Phys. Chem. C, 111 (2007), pp. 16290-16299.*
"Microwave-assisted synthesis of nanocrystalline mesoporous gallium oxide," Chinmay A. Deshmane et al. Microporous and Mesoporous Materials 130 (2010), pp. 97-102.*
"Thermally Stable Nanocrystalline Mesoporous Gallium Oxide Phases," Chinmay A. Deshmane et al. Eur. J. Inorg. Chem. (2009), pp. 3275-3281.*
Prior art search for KR 10-2012-008307.*
"Highly porous gallium oxide with a high CO2 affinity for the photocatalytic conversion of carbon dioxide into methane," Hang-ah Park et al. Journal of Materials Chemistry, 2012, 22, pp. 5304-5307.*

* cited by examiner

*Primary Examiner* — Patricia L Hailey
(74) *Attorney, Agent, or Firm* — Baker & Hostetler LLP

(57) ABSTRACT

The present invention relates to preparation of porous gallium (III) oxide [$Ga_2O_3$] photocatalyst for production of hydrocarbons a porous gallium oxide photocatalyst for production of hydrocarbons, manufactured by the foregoing method, and a process of producing hydrocarbons using the porous gallium oxide photocatalyst for production of hydrocarbons, manufactured by the foregoing method.

8 Claims, 3 Drawing Sheets

METHOD OF MANUFACTURING A POROUS GALLIUM (III) OXIDE PHOTOCATALYST FOR PREPARATION OF HYDROCARBONS

CROSS-REFERENCE TO RELATED APPLICATIONS

This application claims priority from Korean Patent Application No. 10-2012-0008307, filed on Jan. 27, 2012 in the Korean Intellectual Property Office, the entire disclosure of which is incorporated herein by reference.

FIELD OF THE INVENTION

The present invention relates to a method of manufacturing a porous gallium (III) oxide [$Ga_2O_3$] photocatalyst for production of hydrocarbons, and more particularly, to a method of manufacturing a porous gallium (III) oxide photocatalyst for production of hydrocarbons, comprising: adding a base and a surfactant to a solvent and agitating the mixture to prepare a solution containing micelles formed therein; adding a solution containing a gallium precursor to the micelle-containing solution to conduct a reaction; and washing and drying a precipitate obtained by filtering reactants after the reaction, and heating the precipitate to remove the micelles from a surface and an inner part of the precipitate, followed by forming pores therein.

The present invention also relates to a porous gallium oxide photocatalyst for production of hydrocarbons, manufactured by the foregoing method, and a process of producing hydrocarbons using the porous gallium oxide photocatalyst for production of hydrocarbons, manufactured by the foregoing method.

The hydrocarbons described above may include hydrocarbons having 1 to 4 carbon atoms, preferably, aliphatic hydrocarbons having 1 to 4 carbon atoms, and more preferably, methane.

BACKGROUND OF THE INVENTION

Artificial photo-synthesis technologies that use a photocatalyst to produce useful fuel from carbon dioxide and/or conversion of carbon dioxide to the same are now a global issue. Such a method of preparing a useful fuel using carbon dioxide and/or converting carbon dioxide to the same substantially utilizes only water and solar light, therefore, may be the most eco-friendly and sustainable technique. The fuel produced by the foregoing method may include hydrocarbons having 1 to 4 carbon atoms, preferably, aliphatic hydrocarbons having 1 to 4 carbon atoms, and more preferably, methane.

Methane has the simplest form among hydrocarbons, however, is a main component of natural gas generating the largest energy (55.7 kJ/g) per unit mass and hence is generally known as a useful fuel.

In order to convert carbon dioxide ($CO_2$) to methane using solar energy, it is important to use an excellent photocatalyst.

Recently, gallium (III) oxide ($Ga_2O_3$) has attracted worldwide attention since it has superior photo-catalytic properties and high reduction potential to render $CO_2$ to be converted to methane. However, studies on conversion of $CO_2$ to methane using gallium (III) oxide have not yet been reported.

Accordingly, the present invention relates to a method of manufacturing a porous gallium (III) oxide photocatalyst with novel structure and form, and a method for production of hydrocarbons, preferably, aliphatic hydrocarbons having 1 to 4 carbon atoms, and more preferably, methane from $CO_2$ or for conversion of $CO_2$ to any of the foregoing hydrocarbons or methane by using the aforesaid porous gallium (III) oxide photocatalyst.

In this regard, prior arts to which the present invention pertains may include the following:

Grimes et al. have disclosed photo-synthesis wherein titanium dioxide nanotubes ($TiO_2$ nanotubes) synthesized through anodization is used to generate methane from $CO_2$ and water [High-Rate Solar Photocatalytic Conversion of $CO_2$ and Water Vapor to Hydrocarbon fuels, Nano Lett., 2009, 9, 731]. However, it is known that such $TiO_2$ material is less effective in reducing $CO_2$ to produce methane due to a relatively low chemical reduction potential thereof [Toward Solar Fuels: Photocatalytic Conversion of Carbon Dioxide to Hydrocarbons, ACS nano, 2010, 4, 1259].

Further, Tanaka et al. have conducted reduction of $CO_2$ from hydrogen as well as $CO_2$ using a $\beta$-$Ga_2O_3$ photocatalyst, which is known to have high reduction potential [Effect of $H_2$ gas as a reductant on photoreduction of $CO_2$ over a $Ga_2O_3$ Photocatalyst, Chem. Phys. Lett., 2008, 467, 191]. However, it was found that the above photocatalyst did not produce methane, but instead generated carbon monoxide (CO), which is substantially an intermediate stage of the reduction.

SUMMARY OF THE INVENTION

Therefore, an object of the present invention is to provide a method of manufacturing a porous gallium (III) oxide ($Ga_2O_3$) photocatalyst which can produce hydrocarbons, preferably, aliphatic hydrocarbons having 1 to 4 carbon atoms, and more preferably, methane by using carbon dioxide ($CO_2$) and water under a light source with high reaction efficiency and/or productivity; or, otherwise, which can conduct conversion of the above materials (that is, $CO_2$ and water) to the foregoing, that is, hydrocarbons, preferably, aliphatic hydrocarbons having 1 to 4 carbon atoms, and more preferably, methane.

Another object of the present invention is to provide the porous $Ga_2O_3$ photocatalyst for production of hydrocarbons, manufactured by the foregoing method.

Another object of the present invention is to provide a process of producing hydrocarbons using the porous $Ga_2O_3$ photocatalyst for production of hydrocarbons, manufactured by the foregoing method.

According to the present invention, there is a method of manufacturing a porous gallium (III) oxide photocatalyst for production of hydrocarbons, comprising: adding a base and a surfactant to a solvent and agitating the mixture to prepare a solution containing micelles foamed therein ('micelle-containing solution'); adding a solution containing a gallium precursor to the micelle-containing solution to conduct a reaction; and washing and drying a precipitate obtained by filtering reactants after the reaction, and heating the precipitate to remove the micelles from a surface and an inner part of the precipitate, followed by forming pores therein.

The present invention may also provide a porous $Ga_2O_3$ photocatalyst for production of hydrocarbons, manufactured by the foregoing method.

Further, the present invention may provide a process of producing hydrocarbons using the porous $Ga_2O_3$ photocatalyst for production of hydrocarbons, manufactured by the foregoing method.

The porous $Ga_2O_3$ photocatalyst manufactured by the present invention includes pores afforded therein to increase an amount of $CO_2$ adsorption as a product of photo-reaction and, since such a photo-reaction is a reaction occurring at the surface of the $Ga_2O_3$ photocatalyst, an increase in $CO_2$ adsorption on the pores present inside the $Ga_2O_3$ may contribute to improvement in efficiency of the photo-reaction, thereby rendering hydrocarbons, preferably, aliphatic hydrocarbons having 1 to 4 carbon atoms, and more preferably, methane to be produced in large quantities.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
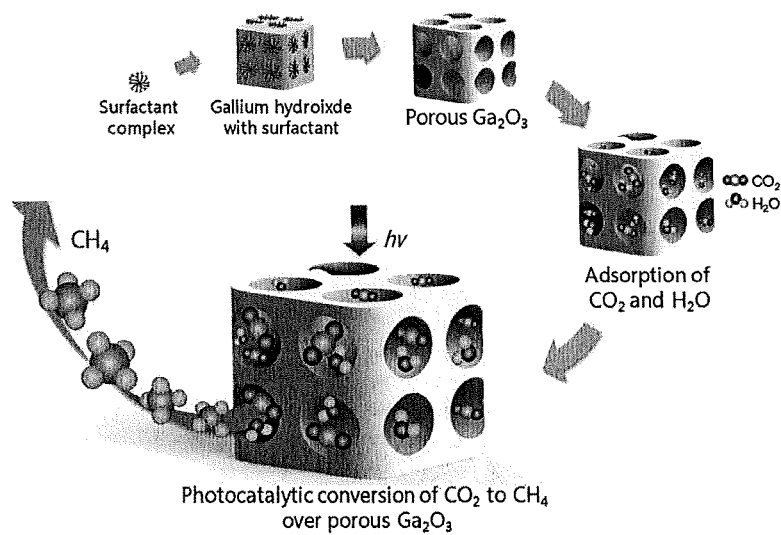
FIG. 1 is schematic views illustrating a method of manufacturing a porous $Ga_2O_3$ photocatalyst and the production of methane as a hydrocarbon from raw materials such as $CO_2$ and water using the manufactured porous $Ga_2O_3$ photocatalyst.

The present invention discloses a method of manufacturing a porous $Ga_2O_3$ photocatalyst used for production of hydrocarbons.

The present invention also discloses a method of manufacturing a porous gallium (III) oxide photocatalyst used for production of hydrocarbons, which includes: adding a base and surfactant to a solvent and agitating the mixture to prepare a solution containing micelles formed therein; adding a solution containing a gallium precursor to the micelle-containing solution to initiate a reaction therebetween; and washing and drying a precipitate obtained by filtering the mixture after the reaction described above, and heating the precipitate to remove the micelles from the surface of the precipitate as well as inside the same while forming pores therein.

In the formation of micelles, a solvent may be purified water ('water').

In the formation of micelles, a solvent may be ethanol.

In the formation of micelles, a solvent may be methanol.

In the formation of micelles, a solvent may include at least one selected from water, ethanol and methanol.

In the formation of micelles, a base may be ammonium hydroxide ($NH_4OH$).

In the formation of micelles, a base may be sodium hydroxide (NaOH).

In the formation of micelles, a base may be potassium hydroxide (KOH)

In the formation of micelles, a base may include at least one selected from $NH_4OH$, NaOH and KOH.

In the formation of micelles, a surfactant may be tetradecyltrimethylammonium bromide (TTAB).

In the formation of micelles, a surfactant may be hexadecyltrimethylammonium bromide (CTAB).

In the formation of micelles, a surfactant may comprise TTAB and CTAB.

In the formation of micelles, agitation may be implemented at 100 to 500 rpm for 30 minutes to 1 hour.

In the formation of micelles, 5 to 10 ml of at least one base selected from $NH_4OH$, NaOH and KOH, and 100 to 300 mg of at least one surfactant selected from TTAB and CTAB may be added to 100 ml of at least one solvent selected from water, ethanol and methanol, followed by agitating the above mixture at 100 to 500 rpm for 30 minutes to 1 hour, to thereby form micelles.

The formation of micelles may further comprise using an additive helpful to form the micelles as a component added to the solvent, other than the base and surfactant described above.

Such an additive helpful to form the micelles may include, for example, 1-dodecanethiol.

Alternatively, the formation of micelles may include adding 5 to 10 ml of at least one base selected from $NH_4OH$, NaOH and KOH, 100 to 300 mg of at least one surfactant selected from TTAB and CTAB and, as an additive helpful to form the micelles, and 0.01 to 0.1 ml of 1-dodecanethiol to 100 ml of at least one solvent selected from water, ethanol and methanol, and then, agitating the above mixture at 100 to 500 rpm for 30 minutes to 1 hour, to thereby form micelles.

The solution containing a gallium precursor may be prepared by adding the gallium precursor to a solvent.

The solution containing a gallium precursor may be a solution prepared by adding at least one gallium precursor selected from gallium nitrate hydrate ($Ga(NO_3)_3 \cdot xH_2O$), gallium sulfate hydrate ($Ga_2(SO_4)_3 \cdot xH_2O$) and gallium perchlorate hydrate ($Ga(ClO_4)_3 \cdot xH_2O$) to a solvent selected from water, ethanol and methanol.

In this regard, the solution containing a gallium precursor may be a solution prepared by adding gallium nitrate hydrate ($Ga(NO_3)_3 \cdot xH_2O$) as the gallium precursor to an ethanol solvent.

More particularly, the solution containing a gallium precursor may be a solution prepared by adding 0.5 to 1.5 g of at least one gallium precursor selected from gallium nitrate hydrate ($Ga(NO_3)_3 \cdot xH_2O$), gallium sulfate hydrate ($Ga_2(SO_4)_3 \cdot xH_2O$) and gallium perchlorate hydrate ($Ga(ClO_4)_3 \cdot xH_2O$) to 100 ml of any one solvent selected from water, ethanol and methanol.

Preferably, the solution containing a gallium precursor may be a solution prepared by adding 0.5 g of gallium nitrate hydrate ($Ga(NO_3)_3 \cdot xH_2O$) to 100 ml of an ethanol solvent.

The prepared gallium precursor-containing solution may be added to a solution containing micelles formed therein, followed by agitating the mixture at 65 to 75° C. and 100 to 500 rpm for 1 to 3 hours to initiate a reaction therebetween.

The gallium precursor-containing solution may be added to a solution containing micelles formed therein, followed by agitating the mixture at 70° C. and 300 rpm for 2 hours to initiate a reaction therebetween.

The precipitate obtained after filtration may be subjected to washing, drying under vacuum and heating at 500 to 700° C. for 5 to 8 hours to remove the micelles from the surface of the precipitate as well as inside the same, thereby resulting in a porous gallium nitride catalyst.

More particularly, the precipitate obtained after filtration may be washed using distilled water and dried under vacuum, followed by heat treatment at 600° C. for 6 hours, to remove the micelles from the surface of the precipitate as well as inside the same, thereby manufacturing a porous gallium nitride catalyst.

FIG. 1 is schematic views illustrating a method of manufacturing a porous gallium oxide photocatalyst according to the present invention, as well as a photo-reaction which is performed using $CO_2$ and water as raw materials under a light source to produce methane and is promoted by the porous gallium oxide photocatalyst manufactured by the foregoing method.

According to the inventive method of manufacturing the porous gallium oxide photocatalyst, a porous gallium oxide photocatalyst having pores formed therein may be prepared using a surfactant, base and nitric acid precursor.

The surfactant may contribute to formation of micelles, the base may reduce the gallium precursor while promoting gelling. When the solution containing a gallium precursor is added to the solution containing the micelles formed therein, a gallium hydroxide phase in which the micelles are contained may be generated.

In this case, heat treatment at a high temperature may burn out the micelles present on the surface of gallium hydroxide as well as inside the same, to thereby remove the micelles. Instead, pores may be formed on the surface of gallium hydroxide as well as inside the same, which are free from the micelles. Moreover, controlling a heat treatment temperature in the range of 500 to 700° C. may convert a gallium phase to $Ga_2O_3$.

The porous $Ga_2O_3$ photocatalyst manufactured according to the foregoing method may produce hydrocarbons from raw materials such as $CO_2$ and water and/or convert the raw materials into hydrocarbons.

The porous $Ga_2O_3$ photocatalyst manufactured according to the foregoing method may conduct reaction using $CO_2$ and water as raw materials under a light source to produce aliphatic hydrocarbons having 1 to 4 carbon atoms and/or convert the raw materials into the foregoing hydrocarbons.

The porous $Ga_2O_3$ photocatalyst manufactured according to the foregoing method may conduct reactions using $CO_2$ and water as raw materials under a light source to produce methane and/or convert the raw materials into methane.

The porous $Ga_2O_3$ photocatalyst manufactured according to the foregoing method may be prepared in a rod shape wherein pores having a diameter of 0.1 to 100 μm are formed.

The porous $Ga_2O_3$ photocatalyst manufactured according to the foregoing method may have a specific surface area (BET) in the range of 40 to 48 $m^2/g$.

The porous $Ga_2O_3$ photocatalyst manufactured according to the foregoing method may have a specific surface area (BET) in the range of 40 to 48 $m^2/g$ as well being prepared in a rod shape wherein pores having a diameter of 0.1 to 100 μm are formed.

As described above, the method of manufacturing a porous $Ga_2O_3$ photocatalyst used for production of hydrocarbons according to the present invention has been practically executed under a variety of conditions and it is expected from the results that, in order to accomplish the purposes of the present invention, the method of manufacturing a porous $Ga_2O_3$ photocatalyst is preferably conducted under such various conditions as described above.

The present invention may include a porous $Ga_2O_3$ photocatalyst used for production of hydrocarbons, manufactured according to the foregoing method.

The porous $Ga_2O_3$ photocatalyst described above may be prepared in a rod shape wherein pores having a diameter of 0.1 to 100 μm are formed.

The porous $Ga_2O_3$ photocatalyst described above may have a specific surface area (BET) in the range of 40 to 48 $m^2/g$.

The porous $Ga_2O_3$ photocatalyst described above may have a specific surface area (BET) in the range of 40 to 48 $m^2/g$ as well being prepared in a rod shape wherein pores having a diameter of 0.1 to 100 μm are formed.

The present invention may further comprise a process of producing hydrocarbons from $CO_2$ and water as raw materials and/or a process of converting the raw materials described above to hydrocarbons through reaction under a light source by using the porous $Ga_2O_3$ photocatalyst used for production of hydrocarbons, which was manufactured according to the foregoing method.

The porous $Ga_2O_3$ photocatalyst described above may render production of aliphatic hydrocarbons having 1 to 4 carbon atoms from $CO_2$ and water as raw materials and/or conversion of the raw materials to the foregoing hydrocarbons, through reaction under a light source.

The porous $Ga_2O_3$ photocatalyst described above may produce methane from $CO_2$ and water as raw materials and/or covert the raw materials to methane, through reaction under a light source.

Such a light source may be solar light or a xenon (Xe) lamp.

Hereinafter, preferred embodiments of the present invention will be described in detail to more concretely understand the present invention with reference to examples, comparative examples, practical examples and experimental examples. However, it will be apparent to those skilled in the art that such embodiments are provided for illustrative purposes and do not limit subject matters to be protected as defined by the appended claims.

EXAMPLE 1

Synthesisis $Ga_2O_3$ Photocatalyst 1.5 mL of $NH_4OH$, 50 mg of tetradecyltrimethylammonium bromide (TTAB) and 0.01 mL of 1-dodecanethiol were added to 25 mL of water at 70° C., and then, the mixture was agitated at 300 rpm for 30 minutes, to thereby form micelles.

A solution of 1 g of gallium nitride hydrate ($Ga(NO_3)_3 \cdot xH_2O$) dissolved in 200 mL of ethanol was added and mixed to the prepared micelle solution, as described above, and then, the mixture was agitated at 70° C. and 300 rpm for 2 hours to render reaction therebetween.

After the reaction described above, a precipitate was filtered, washed using distilled water, dried under vacuum, and subjected to heat treatment at 600° C. for 6 hours to remove the micelles founed on the surface of the precipitate as well as inside the same, thereby generating pores on the surface of the precipitate as well as inside the same, which were free from the micelles. As a result, a porous $Ga_2O_3$ photocatalyst was manufactured.

Practical Example 1

$CO_2$ at 1 atm and 2 mmol of water ($H_2O$) were used as reactants and reacted to produce methane ($CH_4$) in the presence of the porous $Ga_2O_3$ photocatalyst prepared in Example 1 and under a 300 W Xenon lamp (quantity of light: 500 mW/cm$^2$) as a light source.

Photo-reaction in the presence of the porous $Ga_2O_3$ photocatalyst prepared in Example 1 was performed in a closed chamber system and a dead volume thereof was 15.74 mL. In order to introduce a gas and conduct assessment, an inlet valve and an outlet valve were mounted on the above system. The light source was substantially a 300 W Xenon lamp and emitted light through a quartz window provided on the upper part of a reactor. Moreover, an IR cutting filter was used and a reaction quantity of light was 500 mW/cm$^2$.

In the reaction, in order to vaporize water while retaining a temperature at a constant level, a PID temperature control system was used while maintaining the temperature at about 60° C.

The porous $Ga_2O_3$ photocatalyst prepared in Example 1 was loaded in an amount of 50 mg to a glass holder. In order to introduce a reactant, i.e., $CO_2$, the reactor was thoroughly purged using $CO_2$ over 30 minutes and 3 mmol of water as another reactant was introduced using a needle, followed by vaporizing. For assessment of methane as a reaction product, gas chromatography was performed in a column equipped with a thermal conductivity detector (TCD). The column was a 5 A molecular sieve. Using a gas tight syringe, the generated gas was subjected to sampling for analysis by 200 µl of each at constant interval.

Comparative Example $CO_2$ and water ($H_2O$) were used as reactants and reacted to produce methane ($CH_4$) in the presence of a $Ga_2O_3$ photocatalyst commercially available in the market (manufacturer; ALDRICH Com., ref-$Ga_2O_3$) and under a 300 W Xenon lamp (quantity of light: 500 mW/cm$^2$) as a light source.

Photo-reaction in the presence of the above commercially available $Ga_2O_3$ photocatalyst was substantially performed by the same photo-reaction procedure as described in Practical Example 1.

Experimental Example 1

Figure 2:
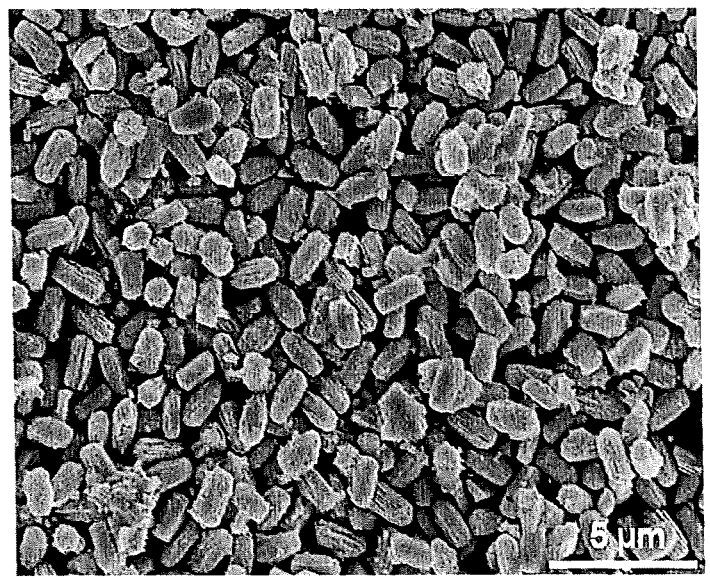
FIG. 2 illustrates an SEM image of the porous $Ga_2O_3$ photocatalyst with low magnification.

The porous $Ga_2O_3$ photocatalyst prepared in Example 1 was measured by low magnification scanning electron microscopy (SEM) and an image thereof is illustrated in FIG. 2.

As shown in FIG. 2, it was found that the porous $Ga_2O_3$ photocatalyst prepared in Example 1 is formed in a rod shape with high nano-scale uniformity of about several hundreds of nanometers.

Experimental Example 2

Figure 3:
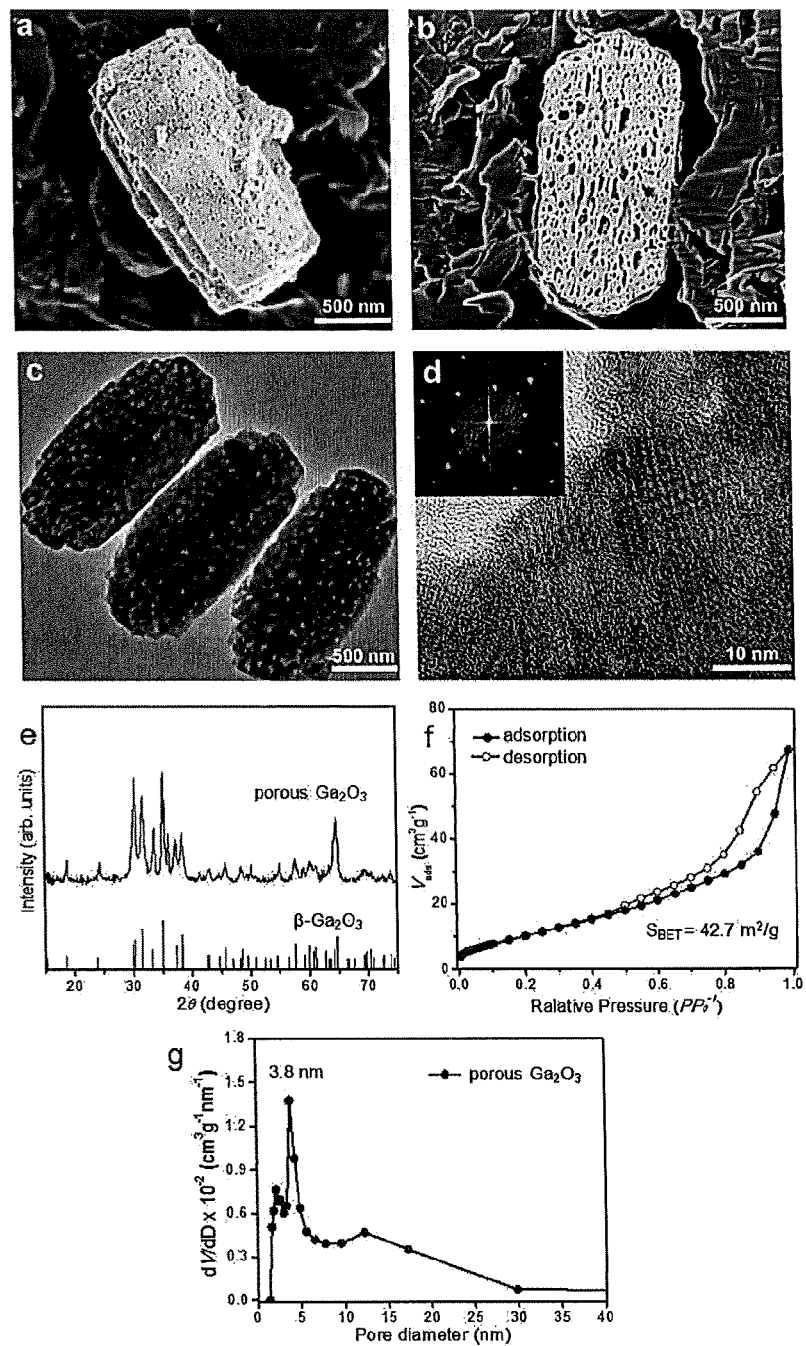
FIG. 3a is an SEM image (top view) of the porous $Ga_2O_3$ photocatalyst.
FIG. 3b is an SEM image illustrating a cross-section of the porous $Ga_2O_3$ photocatalyst.
FIG. 3c is a TEM image of the porous $Ga_2O_3$ photocatalyst with low magnification.
FIG. 3d is a TEM image of the porous $Ga_2O_3$ photocatalyst with high magnification.
FIG. 3e illustrates XRD pattern of the porous $Ga_2O_3$ photocatalyst.
FIG. 3f illustrates nitrogen adsorption of the porous $Ga_2O_3$ photocatalyst.
FIG. 3g illustrates a distribution of pore sizes of the porous $Ga_2O_3$ photocatalyst.

A structure of the porous $Ga_2O_3$ photocatalyst prepared in Example 1 was analyzed and the analyzed results are illustrated in FIG. 3 (from FIGS. 3a to 3G).

More particularly, FIG. 3a is an SEM image of the porous $Ga_2O_3$ photocatalyst wherein very fine pores present on the surface of the photocatalyst can be observed.

FIG. 3b is an SEM image illustrating a cross-section of the porous $Ga_2O_3$ photocatalyst prepared in Example 1, after cutting the cross-section with an ion beam, wherein porous $Ga_2O_3$ particles prepared in Example 1 exhibited a number of pores formed inside the particles as well as on the surface of the same. Such pores may increase adsorption energy of the gas and also increase a specific surface area, a pore volume, or the like. Therefore, when methane is produced by reaction of $CO_2$ and water as raw materials in the presence of the foregoing porous $Ga_2O_3$ photocatalyst and under a light source, or, when the raw materials are converted to methane, the pores may greatly increase adsorption of $CO_2$ and water and hence enhance reactivity, thereby improving productivity of methane.

Furthermore, in order to identify the internal structure of the porous $Ga_2O_3$ photocatalyst prepared in Example 1, transmission electron microscopy (TEM) analysis was performed.

FIG. 3c is a TEM image of the porous $Ga_2O_3$ photocatalyst prepared in Example 1 with low magnification, wherein a number of pores formed in the photocatalyst can be observed.

FIG. 3d is a TEM image of the porous $Ga_2O_3$ photocatalyst prepared in Example 1 with high magnification, wherein micro- and/or meso-pores as well as large ones (that is, macro-pores) present therein can be observed.

For the porous $Ga_2O_3$ photocatalyst prepared in Example 1, in order to identify whether $Ga_2O_3$ has been successfully produced by heat treatment executed to remove the micelles and convert the gallium precursor to $Ga_2O_3$, powder X-ray diffraction (PXRD) was measured and the measured results are shown in FIG. 3e. From FIG. 3e, it can be seen that the porous $Ga_2O_3$ photocatalyst prepared in Example 1 has formed a $\beta$-$Ga_2O_3$ phase.

Moreover, in order to analyze a specific surface area, pore size distribution, etc. of the porous $Ga_2O_3$ photocatalyst prepared in Example 1, a $N_2$ adsorption isotherm graph at 77K was measured and the measured results are shown in FIG. 3f. As a result of estimating the specific surface area of the porous $Ga_2O_3$ photocatalyst prepared in Example 1 using a Brunauer-Emmett-Teller (BET) model, the specific surface area was 42.7 m$^2$/g, which is improved by about 200%, compared to the specific surface area of a bulk $Ga_2O_3$, i.e., about 20.49 m$^2$/g.

Alternatively, the distribution in pore size of the porous $Ga_2O_3$ photocatalyst prepared in Example 1 was assessed using a desorption curve of the $N_2$ adsorption isotherm graph and the assessed results are shown in FIG. 3g. This figure was prepared using a Barrett, Joyner and Halenda (BJH) method (E. P. Barrett, L. G. Joyner, P. P. Halenda, J. Am. Chem. Soc., 1951, 73, 373). From the assessed results in FIG. 3g, it was confirmed that pores with the pore size of 3.8 nm are present in large quantities and, consequently, the porous $Ga_2O_3$ photocatalyst prepared in Example 1 was successfully synthesized.

Experimental Example 3

Figure 4:
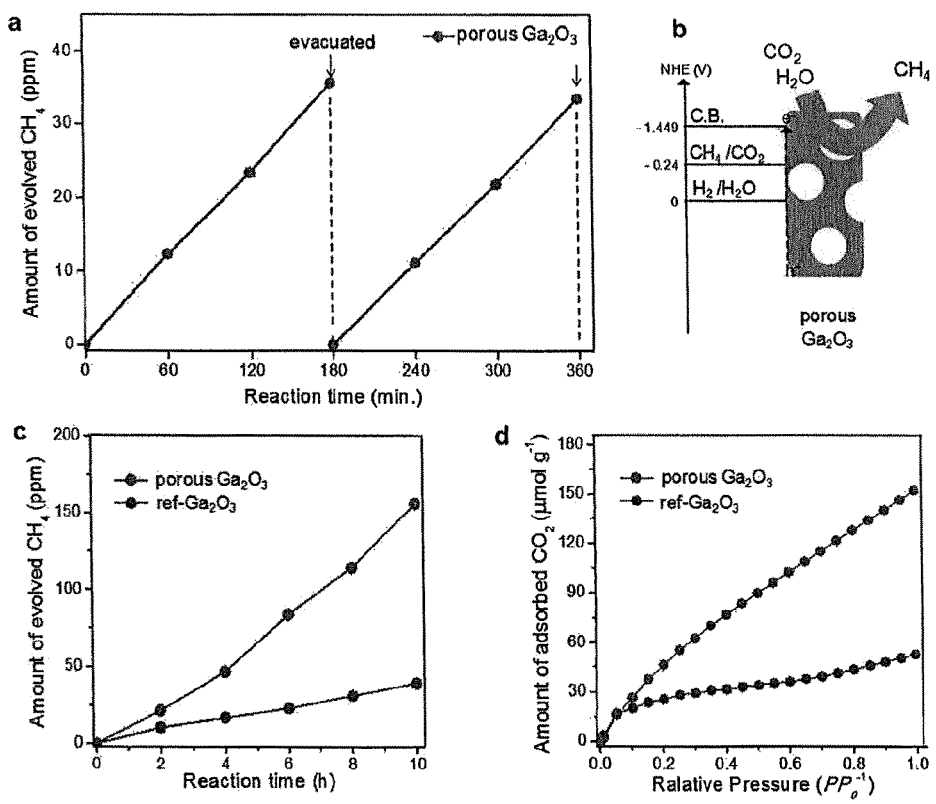
FIG. 4a is graphs illustrating recycling features of the porous $Ga_2O_3$ photocatalyst producing methane from $CO_2$.
FIG. 4b is graphs illustrating redox potential of $CO_2$ and energy band position of $Ga_2O_3$.
FIG. 4c is graphs illustrating photocatalytic properties of the porous $Ga_2O_3$ photocatalyst in regard to methane conversion (10 hours reaction)
FIG. 4d is graphs illustrating analyzed results of $CO_2$ adsorption of the porous $Ga_2O_3$ photocatalyst, compared to a typical $Ga_2O_3$ photocatalyst.

Photo-reaction characteristics of the porous $Ga_2O_3$ photocatalyst prepared in Example 1 were determined through reaction between $CO_2$ and water to produce methane and results thereof are shown in FIG. 4.

FIG. 4a illustrates a result of the reaction between $CO_2$ and water to produce methane using the porous $Ga_2O_3$ photocatalyst prepared in Example 1 described in Practical Example 1, wherein an amount of methane generated per each hour is illustrated. When radiating a light source, $CO_2$ and water reacted together due to the porous $Ga_2O_3$ photocatalyst prepared in Example 1, to hence successfully produce methane. From the foregoing, it can be seen that the produced amount of methane is increased linearly with time. Also, in order to identify recycling features of the porous $Ga_2O_3$ photocatalyst, the reaction was stopped in the middle, while a reactor was evacuated and then set to an initial condition, followed by proceeding the reaction between $CO_2$ and water with the porous $Ga_2O_3$ photocatalyst prepared in Example 1, to thereby produce methane again. As a result of assessing such a production of methane, it was confirmed that the produced amount of methane was substantially identical to that described above before stopping the reaction, thereby demonstrating that the photocatalyst retained its original features. It is considered that such a reaction to produce methane is performed by very high reduction of excited electrons generated during photo-reaction, as illustrated in the band diagram of FIG. 4b, since a conduction band (C.B.) of the porous $Ga_2O_3$ photocatalyst is positioned at a level higher than a reduction potential at which $CO_2$ is converted to methane.

In order to specifically identify methane production features, graphs illustrating photo-reaction executed for about 10 hours are shown in FIG. 4c. In particular, FIG. 4c illustrates results of comparing characteristics of the methane production using the porous $Ga_2O_3$ photocatalyst prepared in Example 1 described in Practical Example 1, with the methane production characteristics if using a typical $Ga_2O_3$ commercially available in the market (available from ALDRICH Com., ref-$Ga_2O_3$). As illustrated in FIG. 4c, when the production of methane was measured using the porous $Ga_2O_3$ photocatalyst prepared in Example 1 after 10 hours of photo-reaction, it was confirmed that a great amount of methane, i.e., 156 ppm had been produced. On the other hand, in the case of using the typical $Ga_2O_3$ (ref-$Ga_2O_3$), an amount of methane production was measured to be about 38 ppm, which is decreased by 400% less than an amount of methane produced using the porous $Ga_2O_3$ photocatalyst prepared in Example 1.

In order to investigate a reason of the improvement in methane production by using the porous $Ga_2O_3$ photocatalyst prepared in Example 1, compared to that obtained if typical $Ga_2O_3$ (ref-$Ga_2O_3$) is used, adsorption of $CO_2$ as a reactant was assessed in relation to different catalysts, respectively. $CO_2$ adsorption was conducted at room temperature. Adsorption isotherm graphs at 0 through 1 atm were determined and results thereof are shown in FIG. 4d. As illustrated in FIG. 4d, it was confirmed that the porous $Ga_2O_3$ photocatalyst prepared in Example 1 exhibited 300% improved $CO_2$ adsorption compared to typical $Ga_2O_3$ (ref-$Ga_2O_3$). Consequently, it may be concluded that improved methane production of the porous $Ga_2O_3$ photocatalyst prepared in Example 1 is based on improvement in $CO_2$ adsorption by pores generated in the porous $Ga_2O_3$ photocatalyst.

EXAMPLE 2

Synthesis of Porous $Ga_2O_3$ Photocatalyst 6 mL of $NH_4OH$, 200 mg of hexadecyltrimethylammonium bromide (CTAB) and 0.04 mL of 1-dodecanethiol were added to 100 mL of water at 70° C., and then, the mixture was agitated at 300 rpm for 30 minutes, to thereby form micelles.

A solution of 1 g of gallium nitrate hydrate ($Ga(NO_3)_3 \cdot xH_2O$) dissolved in 200 mL of ethanol was added and mixed to the prepared micelle solution, as described above, and then, the mixture was agitated at 70° C. and 300 rpm for 2 hours to initiate a reaction therebetween.

After the reaction described above, a precipitate was filtered, washed using distilled water, dried under vacuum, and subjected to heat treatment at 600° C. for 6 hours to remove the micelles formed on the surface of the precipitate as well as inside the same, thereby generating pores on the surface of the precipitate as well as inside the same, which were free from the micelles. As a result, a porous $Ga_2O_3$ photocatalyst was manufactured.

Practical Example 2

$CO_2$ at 1 atm and 2 mmol of water ($H_2O$) were used as reactants and reacted to produce 156 ppm of methane ($CH_4$) in the presence of the porous $Ga_2O_3$ photocatalyst prepared in Example 2 and under a 300 W Xenon lamp (quantity of light: 500 mW/cm$^2$) as a light source.

Photo-reaction in the presence of the porous $Ga_2O_3$ photocatalyst prepared in Example 2 was performed by the same photo-reaction procedure as applied in Practical Example 1.

As is apparent from the foregoing, the porous $Ga_2O_3$ photocatalyst according to the present invention may have advantages of simple manufacturing process and possibility of mass production. In addition, stable photocatalytic characteristics may be successfully attained on the basis of other preferable features, i.e., a large specific surface area, excellent chemical and thermal properties, stable recycling features, and the like. Further, because of high $CO_2$ adsorption and reduction potential, the inventive photocatalyst may be possibly used to produce clean fuels such as methane and/or methanol, from $CO_2$ and water. Moreover, because of high reduction potential, the inventive photocatalyst may also be applied to photocatalyst fields used for production of hydrogen from pure water and/or photocatalyst fields used for reduction of $CO_2$ to CO.

Although preferred embodiments of the present invention have been described above in conjunction with the accompanying examples and experimental examples, those skilled in the art will appreciate that various modifications and alterations are possible without departing from the scope and spirit of the invention, based on the foregoing description and the appended claims.

What is claimed is:

1. A method of manufacturing a porous gallium (III) oxide photocatalyst for production of hydrocarbons, comprising:
    adding a base and a surfactant to a solvent and agitating the mixture to prepare a solution containing micelles formed therein;
    adding a solution containing a gallium precursor to the micelle-containing solution to conduct a reaction; and
    washing and drying a precipitate obtained by filtering reactants after the reaction, and heating the precipitate to remove the micelles from a surface and an inner part of the precipitate, followed by forming pores therein.

2. The method according to claim 1, wherein 5 to 10 ml of at least one base selected from ammonium hydroxide ($NH_4OH$), sodium hydroxide (NaOH) and potassium hydroxide (KOH) and 100 to 300 mg of at least one surfactant selected from tetradecyltrimethylammonium bromide (TTAB) and hexadecyltrimethylammonium bromide (CTAB) are added to 100 ml of any one solvent selected from water, ethanol and methanol; and the mixture is agitated at 100 to 500 rpm for 30 minutes to 1 hour to form the micelles.

3. The method according to claim 2, further adding 0.01 to 0.1 ml of 1-dodecanediol, as an additive helpful to form the micelles, to 100 ml of any one solvent selected from water, ethanol and methanol.

4. The method according to claim 1, wherein the solution containing the gallium precursor comprises a solution prepared by adding 0.5 to 1.5 g of gallium nitrate hydrate ($Ga(NO_3)_3 \cdot xH_2O$) as the gallium precursor to 100 ml of any one solvent selected from water, ethanol and methanol.

5. The method according to claim 1, wherein the reaction is conducted by adding the solution containing the gallium precursor to the micelle-containing solution and agitating at 65 to 75° C. and 100 to 500 rpm for 1 to 3 hours.

6. The method according to claim 1, wherein the precipitate is washed using distilled water and dried under vacuum, followed by heat treatment at 500 to 700° C. for 5 to 8 hours.

7. A porous gallium (III) oxide photocatalyst for production of hydrocarbons, manufactured by the method according to claim 1.

8. The photocatalyst according to claim 7, wherein the porous gallium (III) oxide photocatalyst is prepared in a rod shape having pores with a diameter of 0.1 to 100 μm and has a specific surface area ranging from 40 to 48 $m^2/g$.

* * * * *